United States Patent [19]

Naito et al.

[11] Patent Number: 4,933,329

[45] Date of Patent: Jun. 12, 1990

[54] BIS-S-ALKYLBENZENE DERIVATIVES

[75] Inventors: Youichiro Naito, Kyoto; Yasunari Yamaura, Shiga; Masanori Sugiura, Osaka; Chikara Fukaya, Osaka; Kazumasa Yokoyama, Osaka, all of Japan

[73] Assignee: Green Cross Corporation, Osaka, Japan

[21] Appl. No.: 280,402

[22] Filed: Dec. 6, 1988

[30] Foreign Application Priority Data

Dec. 7, 1987 [JP] Japan ................................ 62-310390

[51] Int. Cl.$^5$ ................... A61K 33/42; A61K 31/495; C07C 125/06; C07D 295/08

[52] U.S. Cl. ..................... 514/130; 514/490; 514/506; 514/507; 514/576; 514/717; 514/718; 514/731; 514/252; 514/826; 558/197; 560/32; 560/135; 560/138; 560/142; 544/396

[58] Field of Search .................. 544/396; 568/14, 15, 568/41, 45, 49, 50, 52, 54, 55; 514/252, 716, 717, 718, 719, 723, 130, 490, 506, 546, 507, 576, 731, 826; 558/197; 560/32, 135, 142, 138

[56] References Cited

U.S. PATENT DOCUMENTS

| | | | |
|---|---|---|---|
| 4,533,753 | 8/1985 | McKinnie et al. | 568/54 |
| 4,547,593 | 10/1985 | Ranken | 568/54 |
| 4,602,113 | 7/1986 | McKinnie et al. | 568/54 |

FOREIGN PATENT DOCUMENTS 0122203 10/1984 European Pat. Off. .
0163270 12/1985 European Pat. Off. .

OTHER PUBLICATIONS

Beck et al, CA 88-190279l(1978).
Kompis et al, CA 91-107996k(1979).
Ranken et al, CA 100-191485c(1984).
McKinnie et al, CA 102-28149d(1985).
Ranken, CA 104-168109g(1986).
Saa et al, CA 109-189942s(1988).
Singh et al, CA 109-230716m(1988).
Saa et al, J. Org. Chem 1988 53, 4263-4273.
Y. Koshihara et al., "Caffeic Acid is a Selective . . . Biosynthesis", Biochimica et Biophysics Acta, 792 (1984) 92-97.

*Primary Examiner*—Cecilia Shen
*Attorney, Agent, or Firm*—Sughrue, Mion, Zinn, Macpeak & Seas

[57] ABSTRACT

Novel bis-S-alkylbenzene derivatives capable of inhibiting lipoxygenase, inparticular, 5-lipoxygenase are disclosed. It is expected that the compounds, which are hardly metabolized in vivo, are highly useful in the treatment and/or prevention of various diseases, including allergic diseases such as asthma, inflammation, myocardial infarction, nephritis, scabies and gout.

8 Claims, No Drawings

BIS-S-ALKYLBENZENE DERIVATIVES

FIELD OF THE INVENTION

This invention relates to novel bis-S-alkylbenzene derivatives which exert an inhibition effect on lipoxygenase, in particular, 5-lipoxygenase, and to a lipoxygenase inhibitor composition containing the same.

BACKGROUND OF THE INVENTION 5-lipoxygenase is an enzyme involved in the in vivo synthesis of leukotrienes and 5-hydroxy-eicosatetraenoic acid (5-HETE). These compounds are believed to be involved in the outbreak of various diseases, including allergic diseases such as asthma, inflammation, myocardial infarction, nephritis, scabies and gout.

Therefore, a compound capable of inhibiting 5-lipoxygenase is useful in the treatment and prevention of various diseases, including allergic diseases such as asthma, inflammation, myocardial infarction, nephritis, scabies and gout.

Examples of compounds capable of inhibiting 5-lipoxygenase include caffeic acid and its methyl ester (cf. Biochim. Biophys. Acta., 792, 92 (1984)). However, the lipoxygenase inhibition effects of these compounds are unsatisfactory.

As a result, the 5-lipoxygenase inhibition effect of caffeic acid has seen enhanced by converting the carboxylic acid moiety thereof into derivatives (cf. EP-A-0163270). However, these derivatives have a dihydroxybenzene structure which causes a disadvantage in that they are liable to be metabolized in vivo.

SUMMARY OF THE INVENTION

Accordingly, the present invention aims at providing benzene derivatives which have an intense inhibition effect on 5-lipoxygenase and is hardly metabolized in vivo.

The above-described object of the present invention has been met by bis-S-alkylbenzene derivatives represented by the following general formula (I) (hereinafter referred to as the "bis S-alkylbenzene derivative (I)").

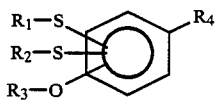  (I)

wherein $R_1$, and $R_2$ each represents an alkyl group; $R_3$ represents a hydrogen atom or an alkyl, an acyl, an alkoxyalkyl, an alkylcarbamoyl or a phosphate group; and $R_4$ represents a group of the following formula:

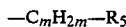

wherein $R_5$ represents a hydrogen atom, an unsubstituted cycloalkyl group or a cycloalkyl group substituted with a hydroxyl group; and m is an integer of 3 to 15; a group of the following formula:

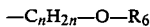

wherein $R_6$ represents a hydrogen atom, an acyl group, an unsubstituted alkyl group or an alkyl group substituted with a hydroxyl group; and n is an integer of 3 to 15; or a benzhydrylpiperazinylalkyl group.

DETAILED DESCRIPTION OF THE INVENTION

In formula (I), each group has the following meaning.

The alkyl group is not particularly restricted, so long as it contains 1 to 4 carbon atoms. Examples thereof include methyl, ethyl, n-propyl, isopropyl, no-butyl, s-butyl and t-butyl groups.

The acyl group is not particularly restricted, so long as it contains 1 to 5 carbon atoms. Examples thereof include formyl, acetyl, propionyl, butyryl and valeryl groups.

The alkoxy group is not particularly restricted, so long as it contains 1 to 4 carbon atoms. Examples thereof include methoxy, ethoxy, n-propoxy, isopropoxy, n-butoxy and t-butoxy groups.

The cycloalkyl group is not particularly restricted, so long as it contains 5 to 7 carbon atoms. Examples thereof include cyclopentyl, cyclohexyl and cycloheptyl groups.

The alkoxy and alkyl moieties of the alkoxyalkyl group are each as defined above. An example thereof is a methoxymethyl group.

The alkyl moiety of the alkylcarbamoyl group is as defined above. Examples thereof include methylcarbamoyl, ethylcarbamoyl and propylcarbamoyl groups.

The alkyl moiety of the benzhydrylpiperazinylalkyl group is as defined above. An example thereof is a benzhydrylpiperazinylmethyl group.

It is preferable that $R_1$ and $R_2$ represent the same alkyl group as each other.

In general formula (I), it is preferable that the substituent $R_2S$ is located at the m-position with respect to the substituent $R_1S$ on the phenyl ring.

It is also preferable that the substituent $R_3O$ is located at the o-position with respect to each of the above-mentioned two substituents.

A compound of the general formula:

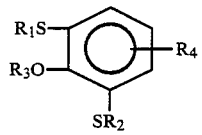

wherein $R_1$, $R_2$, $R_3$ and $R_4$ are as defined above; is particularly preferable.

It is also preferable that the substituents $R_1S$, $R_4$ and $R_2S$ are located at the 2-, 4- and 6-positions respectively, where substituent $R_3O$ is at the 1-position.

A compound of the general formula:

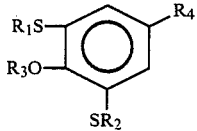

wherein $R_1$, $R_2$, $R_3$ and $R_4$ are as defined above; is particularly preferable.

The bis-S-alkylbenzene derivative (I) of the present invention may be obtained by, for example, the following process:

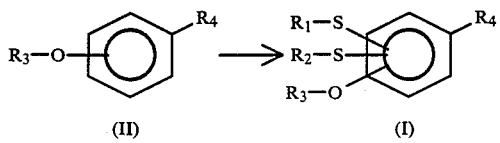

wherein $R_1$, $R_2$, $R_3$ and $R_4$ are as defined above.

Compound (II) is treated with an alkyl lithium, such as n-butyl lithium and then reacted with an alkyl disulfide, wherein each alkyl moiety is as defined above regarding $R_1$ and $R_2$. In this manner, the aimed bis-S-alkylbenzene derivative (I) is obtained.

This reaction may be carried out in an organic solvent, such as tetrahydrofuran or hexane, at a temperature of $-78°$ C. to $5°$ C. for 30 minutes to 5 hours.

Hydroxyl group(s) in compound (II), if any, may be preliminarily protected with appropriate protecting group(s), such as a methoxymethyl group. In this case, the protective group(s) may be eliminated after the completion of the reaction in a conventional manner, such as hydrolysis.

As a result, a bis-S-alkylbenzene derivative of the following general formula:

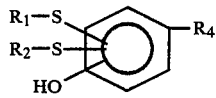

(I-1)

wherein $R_1$, $R_2$, $R_3$ and $R_4$ are as defined above; is obtained. Bis-S-alkylbenzene derivative (I-1), wherein $R_3$ is a hydrogen atom, may be further converted into other bis-S-alkylbenzene derivative wherein $R_3$ is an alkyl, an alkoxyalkyl, an acyl, an alkylcarbamoyl or a phosphate group. This conversion may be carried out via etherification, esterification or carbamoylation, depending on the $R_3$ group to be introduced.

The etherification, i.e., O-alkylation may be carried out by a known method. For example, bis-S-alkylbenzene derivative (I-1) is reacted with a diazoalkane in an organic solvent, such as ether or chloroform, at $-5°$ C. to $5°$ C. for 1 to 10 hours. An alkoxyalkyl group may be introduced into bis-S-alkylbenzene derivative (I-1) by converting the hydroxyl group of compound (I-1) into phenoxide with, for example, sodium hydride and then reacting the obtained product with an alkyl halide alkyl ether. This reaction may be usually carried out in an organic solvent, such as tetrahydrofuran, at $-5°$ C. to $30°$ C. for 10 minutes to 3 hours.

The esterification, i.e., acylation, may be carried out by reacting bis-S-alkylbenzene derivative (I-1) with a carboxylic acid corresponding to the acyl group or a reactive derivative thereof, for example, an acid halide or an acid anhydride. This reaction is favorably carried out in the presence of a catalyst such as triethylamine or pyridine. This reaction may be usually carried out without using any solvent or in an organic solvent, such as chloroform, at $-5°$ C. to $5°$ C. for 1 to 60 minutes.

A phosphate group may be introduced into bis-S-alkylbenzene derivative (I-1) by reacting compound (I-1) with phosphoric acid or a reactive derivative thereof such as phosphorus oxychloride.

An alkylcarbamoyl group may be introduced into bis-S-alkylbenzene derivative (I-1) by reacting compound (I-1) with an alkyl isocyanate. This reaction may be usually carried out in the presence of a catalyst, such as triethlamine, in an organic solvent, such as ethyl acetate, at $-5°$ C. to $5°$ C. for five hours to five days.

Compound (I) thus obtained may be purified in a conventional manner, such as chromatography, with the use of silica gel, distillation under reduced pressure or recrystallization.

Bis-S-alkylbenzene derivative (I) of the present invention has an inhibition effect on 5-lipoxygenase. It inhibits the synthesis of leukotriene and 5-HETE in vivo in mammals including man, horses, dogs, guinea pigs, mice and rats. These facts suggest that it is useful in the treatment and/or prevention of various diseases including allergic diseases such as asthma, inflammation, myocardial infarction, nephritis, scabies and gout.

Further, the metabolism of bis-S-alkylbenzene derivative (I) of the present invention in vivo is suppressed, compared with that of known dihydroxybenzene derivatives. Thus, it is expected that the pharmaceutical effects of the former are enhanced and sustained.

Bis-S-alkylbenzene derivative (I) of the present invention may be orally or parenterally administered either as such or in the form of a preparation together with appropriate and pharmaceutically acceptable carrier(s).

The preparation may be in any conventional form, such as tablets, capsules including soft-capsules and microcapsules, powders, suppositories, injections, ointments, syrups or inhalations.

Bis-S-alkylbenzene derivative (I) of the present invention may be orally administered to an adult in a dose of, for example, 10 to 300 mg once or several times per day. As a matter of course, the dose may vary depending on the age, body weight and/or the condition and reaction against the treatment.

To further illustrate the present invention, and not by way of limitation, the following Examples will be given.

EXAMPLE 1

(1) Synthesis of 8-(4-methoxymethoxyphenyl)octanol:

To a suspension comprising 1.0 g of sodium hydride in 40 ml of dry tetrahydrofuran, 5.27 g of 8-(4-hydroxyphenyl)octanol dissolved in 50 ml of dry tetrahydrofuran was added dropwise at 0° C. The resulting mixture was stirred at room temperature for 30 minutes and then cooled to 0° C. again. Subsequently, 2.1 ml of chloromethyl methyl ether was added dropwise thereto. After stirring at room temperature for 30 minutes, the mixture was cooled to 0° C. and ice and a saturated aqueous solution of sodium bicarbonate were added thereto. The resulting mixture was then extracted with ethyl acetate. The extract was concentrated and subjected to column chromatography (silica gel, ethyl acetate: hexane=1-:3–1:2). As a result, 4.05 g of the desired compound was obtained (yield: 66%).

(2) Synthesis of 8-(4-methoxymethoxyphenyl)octyltetrahydro-2H-pyran-2-yl ether:

5.85 g of product obtained in (1) above was dissolved in 2.4 ml of dihydropyran and 50 ml of dichloromethane. A small amount of p-toluenesulfonic acid (about 100 mg) was added to the obtained solution at 0° C. and stirred at room temperature for 20 minutes. After the completion of the reaction, 0.1 ml of triethylamine was added thereto and the resulting mixture was concentrated and subjected to column chromatography (silica gel, ethyl acetate: hexane=1:30–1:10). As a result, the desired compound was quantitatively obtained.

(3) Synthesis of 8-{3,5-bis(methylthio)-4-methoxymethoxyphenyl}-octyl-tetrahydro-2H-pyran-2-yl ether:

1.76 g of the product obtained in (2) above was dissolved in 15 ml of dry tetrahydrofuran. 3.7 ml of n-butyl lithium was added dropwise to the obtained solution at 0° C. and stirred at 0° C. for 30 minutes. Then, 0.49 ml of dimethyl disulfide was added thereto dropwise and stirred at 0° C. for additional 30 minutes. This procedure was repeated and the resulting mixture was extracted with a mixture of ice, water and ether. After concentrating the extract, the desired compound was obtained.

(4) Synthesis of 8-{3,5-bis(methylthio)-4-hydroxyphenyl}octanol (compound 1):

The crude product obtained in (3) above, 20 ml of dioxane and 10 ml of 1N hydrochloric acid were mixed together and heated under reflux for one hour. After the completion of the reaction, the resulting mixture was extracted with ethyl acetate. The extract was concentrated and subjected to column chromatography (silica gel, ethyl acetate: hexane=1:5–1:2) and then to high performance liquid Chromatography ($C_{18}$ reverse phase system, 70% aqueous acetonitrile). As a result, 690 mg of the desired compound was obtained (48% yield).

$^1$H-NMR (CDCl$_3$) δ:1.3 1.8 (m, 12H), 2.45 (s, 6H), 2.57 (t, J=7.4 Hz, 2H), 3.69 (t, J=6.4 Hz, 2H), 6.99 (s, 1H) and 7.12 (2, 2H) ppm.

IR (neat): 3400, 1570 cm$^{-1}$.

EXAMPLE 2

Synthesis of 8-{3,5-bis(methylthio)-4-methoxymethoxyphenyl}octanol:

A solution comprising the product obtained in Example 1-(3), 100 ml of dry methanol and a small amount of p-toluenesulfonic acid (about 100 mg) were stirred together at 40° C. for 30 minutes. After the completion of the reaction, 0.05 ml of triethylamine was added thereto. The obtained mixture was concentrated and subjected to column chromatography (silica gel, ethyl acetate: hexane=1:3–1:1) and then to high performance liquid chromatography ($C_{18}$ reverse phase system, 70% aqueous acetonitrile). As a result, 0.85 g of the desired compound was obtained (yield: 16%).

$^1$H-NMR (CDCl$_3$) δ: 1.2–1.7 (m, 12H), 2.42 (s, 6H), 2.55 (t, J=7.4 Hz, 2H), 3.63 (t, J=6.4 Hz, 2H), 3.70 (s, 3H), 5.12 (s, 2H) and 6.77 (s, 2H) ppm.

IR (neat) : 3350, 1555 cm$^{-1}$.

EXAMPLE 3

Synthesis of 8-{3,5-bis(methylthio)-4-methoxyphenyl}octanol:

320 mg of compound 1 was dissolved in chloroform and 10 ml of a solution of diazomethane in ether (about 0.5M) was added thereto dropwise at 0° C. After stirring at 0° C. for 6 hours, several drops of acetic acid were added thereto. After the completion of the reaction, the mixture was extracted with ether. The extract was concentrated and subjected to column chyromatography (silica gel, ethyl acetate: hexane=1:5–1:4). As a result, 206 mg of the desired compound was obtained (yield: 62%).

$^1$H-NMR (CDCl$_3$) δ: 1.2–1.7 (m, 12H), 2.42 (s, 6H), 2.54 (t, J=7.4 Hz, 2H), 3.63 (t, J=6.6 Hz, 2H), 3.66 (s, 3H) and 6.75 (s, 2H) ppm.

IR (neat): 3350, 1550 cm$^{-1}$.

EXAMPLE 4

Synthesis of 2,6-bis(methylthio)-4-(8-hydroxyoctyl)phenyl-N-methyl carbamate:

To a solution comprising 71 mg of compound 1, 3 ml of ethyl acetate and several drops of methyl isocyanate, one drop of triethylamine was added at 0° C. and stirred at the same temperature for 5 hours. After the completion of the reaction, the resulting mixture was extracted with ethyl acetate. The extract was concentrated and subjected to column chromatography (silica gel, ethyl acetate: hexane=1:3–1:1). As a result, 58 mg of the desired compound was obtained (yield: 69%).

$^1$H-NMR (CDCl$_3$) δ: 1.2–1.7 (m, 12H), 2.42 (s, 6H), 2.57 (t, J=7.4 Hz, 2H), 2.92 (d, J=4.8 Hz, 3H), 3.62 (t, J=6.4 Hz, 2H), 5.15 (m, 1H) and 6.64 (s, 2H) ppm.

IR (neat): 3500, 3350, 1725 and 1570 cm$-1$.

EXAMPLE 5

Synthesis of 8-{2,6-bis(methylthio)-4-acetoxyphenyl}octyl acetate:

To a solution comprising 190 mg of compound 1, 5 ml of chloroform and 0.1 ml of triethylamine, 0.2 ml of acetyl chloride was added at 0° C. and stirred at room temperature for 10 minutes. After the completion of the reaction, 3 ml of 0.1N hydrochloric acid was added thereto and the obtained mixture was extracted with ethyl acetate. The extract was concentrated and subjected to column chromatography (silica gel, ethyl acetate: hexane=1:10–1:9). As a result, 140 mg of the desired compound was obtained (yield: 58%).

$^1$H-NMR (CDCl$_3$) δ: 1.2–1.7 (m, 12H), 2.04 (s, 3H), 2.36 (s, 3H), 2.47 (s, 6H), 2.58 (t, J=7.4 Hz, 2H), 4.05 (t, J=6.6 Hz, 2H) and 6.87 (s, 2H) ppm.

IR (neat): 1765, 1725 and 1565 cm$^{-1}$.

EXAMPLE 6

(1) Synthesis of 2,6-bis(methylthio)-4-octylphenylmethoxyethyl ether:

The procedure of Example 1-(3) was repeated except using 4-octylphenyl methoxymethyl ether. As a result, 1.9 g of the desired was obtained (yield: 40%).

$^1$H-NMR (CDCl$_3$) δ: 0.88 (t, J=6.2 Hz, 3H), 1.1–1.8 (m, 12H), 2.42 (s, 6H), 2.55 (t, J=7.4 Hz, 2H), 3.70 (s, 2H), 5.12 (s, 2H) and 6.77 (s, 2H) ppm.

IR (neat): 1555 cm$^{-1}$.

(2) Synthesis of 2,6-bis(methylthio)-4-octylphenol (compound 2):

To the crude product obtained in (1) above, 40 ml of dioxane and 20 ml of 1N hydrochloric acid were added and the obtained mixture was heated under reflux for 90 minutes. After the completion of the reaction, the mixture was cooled and extracted with ether. The extract was concentrated and subjected to column chromatography (silica gel, ether: hexane=1:60–1:20) and then to high performance liquid chromatography ($C_{18}$ reverse phase system, 93% aqueous acetonitrile). As a result, 2.4 g of the desired compound was obtained (yield: 51%).

$^1$H-NMR (CDCl$_3$) δ: 0.88 (t, J 6.0 Hz, 3H), 1.1–1.7(m, 12H), 2.39 (s, 6H), 2.51 (t, J=7.4 Hz, 2H), 6.89 (s, 1H) and 7.06 (s, 2H) ppm.

IR (neat): 3380, 1570, 1650 and 1450 cm$^{-1}$.

EXAMPLE 7

Synthesis of 2,6-bis(methylthio)-4-octylanisole:

180 mg of compound 2 was treated according to the procedure of Example 3. As a result, 104 mg of the desired compound was obtained (yield: 58%).

$^1$H-NMR (CDCl$_3$) δ: 0.88 (t, J=6.2 Hz, 3H), 1.1–1.7 (m, 12H), 2.42 (s, 6H), 2.55 (t, J=7.2 Hz, 2H), 3.86 (s, 1H) and 6.75 (s, 2H) ppm.

IR (neat): 1550 cm$^{-1}$.

EXAMPLE 8

Synthesis of 2,6-bis(methylthio)-4-octylphenyl-N-isopropyl carbamate:

To a solution comprising 104 mg of compound 2, 3 ml of ether and 60 mg of isopropyl isocyanate, four drops of triethylamine were added at 0° C. and stirred at room temperature for 2 days. After the completion of the reaction, the obtained mixture was extracted with ether. The extract was concentrated and subjected to column chromatography (silica gel, ether acetate: hexane=1:10–1:6.5). As a result, 61 mg of the desired compound was obtained (yield: 46%).

$^1$H-NMR (CDCl$_3$) δ: 0.88 (t, J=6.2 Hz, 3H), 1.1–1.7 (m, 18H), 2.42 (s, 6H), 2.57 (t, J=7.3 Hz, 2H), 3.8–4.1 (m, 1H), 4.98 (d, J 8Hz, 1H) and 6.83 (s, 2H) ppm.

IR (KBr): 3320, 1715, 1570, and 1530 cm$^{-1}$.

EXAMPLE 9

Synthesis of 2,6-bis(methylthio)-4-octylphenyl-N-methyl carbonate:

The procedure of Example 8 was repeated except that the isopropyl isocyanate was replaced with methyl isocyanate. As a result, the desired compound was obtained (yield: 81%).

$^1$H-NMR (CDCl$_3$) δ: 0.88 (t, J=6.2 Hz, 3H), 1.1–1.7 (m, 12H), 2.42 (s, 6H), 2.57 (t, J=7.4 Hz, 2H), 2.92 (d., J=4.8 Hz, 3H), 5.10 (m, 1H) and 6.84 (s, 2H) ppm.

IR (KBr): 3310, 1725 and 1570 cm$^{-1}$.

EXAMPLE 10

Synthesis of 2,6-bis(methylthio)-4-octylphenyl acetate:

The procedure of Example 5 was repeated except that compound 2 was used. As a result, 98 mg of the desired compound was obtained (yield: 58%).

$^1$H-NMR (CDCl$_3$) δ: 0.88 (t, J=6.2 Hz, 3H), 1.1–1.7 (m, 12H), 2.35 (s, 6H), 2.41 (s, H), 2.57 (t, J 7.4 Hz, 2H), and 6.87 (s, 2H) ppm.

IR (neat): 1770 and 1570 cm$^{-1}$.

EXAMPLE 11

Synthesis of 2,6-bis(methylthio)-4-octylphenyl phosphate:

To 0.24 ml of phosphorus oxychloride dissolved in 5 ml of dry ether at 0° C., 0.36 ml of triethylamine and 515 mg of compound 2 were added. The suspension thus obtained was stirred at 0° C. for 10 minutes and then at room temperature for 30 minutes to thereby concentrate the same. To the residue, 5 ml of dioxane and 10 ml of 0.5M sodium acetate were added. The obtained mixture was stirred at room temperature for 2 hours. After the completion of the reaction, the mixture was extracted with ether. The extract was recrystallized from ether-hexane (3:20) . As a result, 420 mg of the desired compound was obtained (yield: 70%). m.p.: 96°–98° C.

$^1$H-NMR (CDCl$_3$) δ: 0.88 (t, J=6.2 Hz, 3H), 1.1–1.7 (m, 12H), 2.39 (s, 6H), 2.52 (t, J=7.2 Hz, 2H), 6.85 s, 2H) and 8.92 (s, 2H) ppm.

IR (KBr): 3520, 2300, 1560 and 950 cm$^{-1}$.

EXAMPLE 12

(1) Synthesis of 4-[5-(4-methoxymethoxyphenyl)pentyl]cyclohexanol:

1.25 g of 4-[5-(4-hydroxyphenyl)pentyl]cyclohexanol was treated according to the procedure of Example 1-(1). After conducting column chromatography (silica gel, ethyl acetate: hexane=1:4), 400 mg of the cis-form the above compound (yield: 32%) and 473 mg of the trans-form of the above compound (yield: 32%) were obtained.

(2) Synthesis of cis-4-[5-(3,5-bis(methylthio)-4-hydroxyphenyl)pentyl]-cyclohexanol:

400 mg of cis-product obtained in (1) above was treated according to the procedures of Example 1-(2) to (4). As a result, 228 mg of the desired compound was obtained (yield: 56%)

$^1$H-NMR (CDCl$_3$) δ: 1.2–1.8 (m, 18H), 2.40 (s, 6H), 2.51 (t, J=7.6 Hz, 2H), 3.95 (m, 1H), 6.90 (s, 1H) and 7.06 (s, 2H) ppm.

IR (neat): 3550, 1450, and 1225 cm$^{-1}$.

EXAMPLE 13

Synthesis of trans-4-[5-(3,5-bis(methylthio)-4-hydroxyphenyl)pentyl]cyclohexanol:

437 mg of the trans-product obtained in Example 12-(1) was treated according to the procedure of Example 12-(2). As a result, 138 mg of the desired compound was obtained (yield: 25%)

$^1$H-NMR (CDCl$_3$) δ: 0.8–2.0 (m, 18H), 2.39 (s, 6H), 2.51 (t, J=7.6 Hz, 2H), 3.54 (tt, J=10.8, 4.2 Hz, 1H), 6.90 (s, 1H) and 7.06 (s, 2H) ppm.

IR (KBr): 3350, 1450, and 1227 cm$^{-1}$.

EXAMPLE 14

Synthesis of 2,6-bis(methylthio)-4-(8-methoxyoctyl) phenol::

(1) Synthesis of 8-(4-benzyloxyphenyl)octanol:

A suspension comprising 3.0 g of 8-(4-hydroxyphenyl)octanol, 3.0 g of anhydrous potassium carbonate, 50 ml of dry acetone and 1.9 ml of benzyl bromide was heated under reflux for 16 hours. After the completion of the reaction, the potassium carbonate was filtered off and the filtrate was concentrated on an evaporator. The white solid thus obtained was precipitated from chloroform-hexane (1:4). As a result, 3.0 g of the desired compound was obtained (yield: 71%).

(2) Synthesis of 4-(8-methoxyoctyl)phenyl benzyl ether:

To a solution comprising 1.4 g of the product obtained in (1) above, 10 ml of dry dimethylsulfoxide and 1.56 ml of methyl iodide, 0.6 g of 60% sodium hydride was added. The obtained mixture was allowed to react in a water bath at 60° C. After 30 minutes, the reaction mixture was cooled to room temperature and extracted with 200 ml of ether. After distilling off the solvent, the residue was subjected to column chromatography (silica gel, ethyl acetate: hexane=1:20–1:10). As a result, 1.20 g of the desired compound was obtained (yield: 82%).

(3) Synthesis of 4-(8-methoxyoctyl)phenol:

A suspension comprising 1.2g of the product obtained in (2) above, 30 ml of ethyl acetate and 0.5 g of 10% palladium carbon was stirred under a hydrogen atmosphere at room temperature for 15 hours. After the completion of the reaction, the palladium carbon was filtered off and the filtrate was concentrated. As a result, 0.89 g of the desired compound was quantitatively obtained.

(4) Synthesis of 4-(8-methoxyoctyl)phenyl methoxymethyl ether:

0.89 g of the product obtained in (3) above was treated according to the procedure of Example 1-(1). As a result, 783 mg of the desired compound was obtained (yield: 60%).

(5) Synthesis of 2,6-bis(methylthio)-4-(8-methoxyoctyl)phenylmethoxymethyl ether:

770 mg of the product obtained in (4) above was treated according to the procedure of Example 1-(3). The crude product thus obtained was subjected to the process described below.

(6) Synthesis of 2,6-bis(methylthio)-4-(8-methoxyoctyl)phenol:

The crude product thus obtained in (5) above was treated according to the procedure of Example 1-(4). As a result, 400 mg of the desired compound was obtained (yield based on product (4): 44%).

$^1$H-NMR (CDCl$_3$) δ: 1.3–1.7 (m, 12H), 2.39 (s, 6H), 2.51 (t, J=7.4 Hz, 2H), 3.33 (s, 3H), 3.36 (t, J=6.4 Hz, 2H), 6.91 (s, 1H) and 7.05 (s, 2H) ppm.

IR (neat): 3400, 1570 and 1455 cm$^{-1}$.

EXAMPLE 15

Synthesis of 2,6-bis(methylthio)-4-{8-(2-hydroxyethoxy)octyl]-phenol:

(1) Synthesis of 4-[8-{2-(tetrahydro-2H-pyran-2-yloxy)ethoxy) octyl]phenyl benzyl ether:

1.23 g of the product obtained in Example 14-(1) was treated according to the procedure of Example 14-(2) except that the methyl iodide was replaced with 2.6 g of 2-(2-bromoethoxy)-tetrahydro-2H-pyran. As a result, 1.26 g of the desired compound was obtained (yield: 73%)

(2) Synthesis of 4-[8-{2-(tetrahydro-2H-pyran-2-yloxy)ethoxy}octyl]-phenol:

1.26 g of the product obtained in (1) above was treated according to the procedure of Example 14-(3). As a result, 0.86 g of the desired compound was obtained (yield: 86%).

(3) Synthesis of 4-[8-{2-(tetrahydro-2H-pyran-2-yloxy)ethoxy}octyl]-phenylmethoxymethyl ether:

The product obtained in (2) above was treated according to the procedure of Example 14-(4). As a result, 710 mg of the desired compound was obtained (yield: 75%).

(4) Synthesis of 2,6-bis(methylthio)-4-[8-{2-(tetrahydro2H-pyran-2-yloxy)-ethoxy}octyl]phenylmethoxymethoxy ether:

1.55 g of the product obtained in (3) above was treated according to the procedure of Example 14-(5). The crude product thus obtained was subjected to the process described below.

(5) Synthesis of 2,6-bis(methylthio)-4-{8-(2-hydroxyethoxy)octyl} phenol:

The crude product obtained in (4) above was treated according to the procedure of Example 14-(6). As a result, 550 mg of the desired compound was obtained (yield: 39%).

$^1$H-NMR (CDCl$_3$) δ: 1.2–1.7 (m, 12H), 2.13 (s, 6H), 2.39 (s, 6H), 2.51 (t, J=7.2 Hz, 2H), 3.4–3.6 (m, 4H), 3.7–3.75 (m, 2H), 6.92 (s, 1H) and 7.06 (s, 2H) ppm.

IR (neat): 3350, 1555 and 1445 cm$^{-1}$.

EXAMPLE 16

(1) Synthesis of 3, 5-bis(methylthio)-4-methoxymethoxybenzaldehyde propyleneacetal:

5.4 g of 4-methoxymethoxybenzaldehyde propyleneacetal, which had been obtained by methoxylating and propylene-acetalating p-hydroxybenzaldehyde, was treated according to the procedure of Example 1-(3). As a result, 4.2 g of the desired compound was obtained (yield: 55%).

(2) Synthesis of 3,5-bis(methylthio)-4-methoxymethoxybenzaldehyde:

A solution comprising 4.2 g of the product obtained in (1) above, 20 ml of dioxane and 8 ml of 1N hydrochloric acid was stirred at 0° C. for 5 minutes and then at room temperature for 4 hours. After the completion of the reaction, the obtained mixture was extracted with 400 ml of ethyl acetate. The extract was subjected to column chromatography (silica gel, ethyl acetate: hexane=1:5–1:3). As a result, 2.0 g of the desired compound was obtained (yield: 59%).

(3) Synthesis of 1-{3,5-bis(methylthio)-4-methoxymethoxyphenylmethyl}-4-(1,1-diphenylmethyl)piperazine:

To a solution comprising 1.0 g of the product obtained in (2), above, 1.07 g of diphenylmethylpiperazine, 20 ml of methanol and 10 ml of tetrahydrofuran, 268 mg of sodium cyanoborohydride and 2 ml of ethanol were added. The resulting mixture was stirred for 1.5 hours. After the completion of the reaction, the mixture was extracted with ethyl acetate and chloroform. The extract was concentrated and subjected to column chromatography (silica gel, ethyl acetate: hexane=1:5–1:2). As a result, 550 mg of the desired compound was obtained (yield: 29%).

(4) Synthesis of 1-13,5-bis(methylthio)-4-hydroxyphenylmethyl}-4-(1,1-diphenyl-methyl)piperazine:

550 mg of the product obtained in (3) above was treated according to the procedure of Example 1-(4). As a result, 400 mg of the desired compound was obtained (yield: 88%). m.p.": 85°–87° C.

$^1$H-NMR (CDCl$_3$) δ: 2.37 (s, 6H), 2.4–2.45 (m, 8H), 3.42 (s, 2H), 4.22 (s, 1H) and 7.1–7.6 (m, 12H) ppm.

IR (Kbr): 3370, 1595 and 1555 cm$^{-1}$.

EXAMPLE 17

Synthesis of 1-{3,5-bis(sec-butylthio)-4-hydroxyphenylmethyl}-4-(1,1-diphenylmethyl)piperazine:

(1) Synthesis of 1-{3,5-bis(sec-butylthio)-4-hydroxyphenylmethyl}-4-(1,1-diphenylmethyl) piperazine:

1.17 g of 3,5-bis(sec-butylthio)-4-methoxymethoxybenzaldehyde, which had been obtained according to the procedures of Example 16-(1) and (2) except that the dimethyldisulfide was replaced with diisobutyldisulfide, was treated according to the procedure of Example 16-(3). As a result, 460 mg of the desired compound was obtained (yield: 23%).

(2) Synthesis of 1-{3,5-bis(sec-butylthio)-4-hydroxyphenylmethyl}-4-{1,1-diphenylmethyl) piperazine:

460 mg of the product obtained in the (1) above was treated according to the procedures of Example 16-(4). As a result, 300 mg of the desired compound was obtained (yield: 81%).

$^1$H-NMR (CDCl$_3$) δ: 0.99 (t, J=7.4 Hz, 6H), 1.21 (d, J=7.4 Hz, 6H), 1.4–1.8 (m, 4H), 2.3–2.5 (m. 8H), 3.0–3.3 (m, 2H), 3.40 (2. 2H), 4.21 (s, 1H) and 7.1–7.5 (m, 12H) ppm.

IR (neat): 3330, 1595 and 1485 cm$^{-1}$.

While the invention has been described in detail and with reference to specific embodiments thereof, it will be apparent to one skilled in the art that various changes and modifications can be made therein without departing from the spirit and scope thereof.

What is claimed is:

1. A bis-S-alkylbenzene derivative represented by the following formula (I):

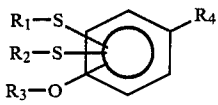

(I)

wherein $R_1$ and $R_2$ each represents a $C_1$–$C_4$ alkyl group; $R_3$ represents a hydrogen atom or a $C_1$–$C_4$ alkyl, a $C_1$–$C_5$ acyl, a $C_1$–$C_4$alkoxy-$C_1$–$C_4$alkyl, a $C_1$–$C_4$ alkylcarbamoyl or a phosphate group: and $R_4$ represents a group of the following formula:

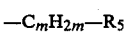

wherein $R_5$ represents a hydrogen atom, an unsubstituted $C_5$–$C_7$ cycloalkyl group, or a $C_5$–$C_7$ cycloalkyl group substituted with a hydroxyl group; and m is an integer of 3 to I5; a group of the following formula:

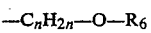

wherein $R_6$ represents a hydrogen atom, a $C_1$–$C_5$ acyl group, an unsubstituted $C_1$–$C_4$ alkyl group, or a $C_1$–$C_4$ alkyl group substituted with a hydroxyl group; and n is an integer of 3 to 15; or a benzhydrylpiperazinyl-$C_1$–$C_4$alkyl group.

2. The bis-S-alkylbenzene derivative as claimed in claim 1, wherein $R_1$ and $R_2$ are the same and represent said alkyl group.

3. The bis-S-alkylbenzene derivative as claimed in claim 1, wherein $R_2S$ is located at the m-position with respect to $R_1S$.

4. The bis-S-alkylbenzene derivative as claimed in claim 1, wherein $R_3O$ is located at the o-position with respect to $R_2S$ and $R_1S$.

5. The bis-S-alkylbenzene derivative as claimed in claim 1, wherein $R_1S$, $R_4$ and $R_2S$ are located at 2-, 4- and 6-positions, respectively, when $R_3O$ is at the 1-position.

6. A method for treatment, prevention or both of an allergic disease comprising administering the bis-S-alkylbenzene derivative of claim 1 to a subject.

7. The method as claimed in claim 6, wherein said compound is administered at a dose of 10 to 300 mg once or several times per day.

8. A lipoxygenase inhibitor composition comprising the bis-S-alkylbenzene derivative of claim 1 as active ingredient in an amount effective to inhibit 5-lipoxygenase and a pharmaceutically acceptable carrier.

* * * * *